(12) United States Patent
Takahashi

(10) Patent No.: US 10,460,882 B2
(45) Date of Patent: Oct. 29, 2019

(54) ELECTROLYTE SOLUTION AND ELECTROCHEMICAL DEVICE

(71) Applicant: DAIKIN INDUSTRIES, LTD., Osaka-shi, Osaka (JP)

(72) Inventor: Kenzou Takahashi, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 256 days.

(21) Appl. No.: 15/517,268

(22) PCT Filed: Oct. 22, 2015

(86) PCT No.: PCT/JP2015/079866
§ 371 (c)(1),
(2) Date: Apr. 6, 2017

(87) PCT Pub. No.: WO2016/068022
PCT Pub. Date: May 6, 2016

(65) Prior Publication Data
US 2017/0309412 A1  Oct. 26, 2017

(30) Foreign Application Priority Data

Oct. 30, 2014  (JP) ................................ 2014-221683

(51) Int. Cl.
| | | |
|---|---|---|
| *H01G 11/62* | (2013.01) | |
| *H01G 11/64* | (2013.01) | |
| *H01M 10/0567* | (2010.01) | |
| *H01M 10/0569* | (2010.01) | |
| *C07C 211/63* | (2006.01) | |
| *H01G 11/28* | (2013.01) | |
| *C01B 35/06* | (2006.01) | |
| *C07D 207/00* | (2006.01) | |
| *C07D 209/04* | (2006.01) | |
| *C07D 211/00* | (2006.01) | |

(52) U.S. Cl.
CPC ............ *H01G 11/62* (2013.01); *C07C 211/63* (2013.01); *H01G 11/28* (2013.01); *H01G 11/64* (2013.01); *H01M 10/0567* (2013.01); *H01M 10/0569* (2013.01); *C01B 35/063* (2013.01); *C07D 207/00* (2013.01); *C07D 209/04* (2013.01); *C07D 211/00* (2013.01); *H01M 2300/0028* (2013.01); *Y02E 60/13* (2013.01)

(58) Field of Classification Search
CPC ........ H01G 11/64; H01G 11/62; H01G 11/60; H01M 10/0567; H01M 10/0568; H01M 10/0569; H01M 2300/0028
See application file for complete search history.

(56) References Cited

U.S. PATENT DOCUMENTS

| | | | | | |
|---|---|---|---|---|---|
| 3,562,017 A | * | 2/1971 | Lyall | ....................... | H01M 6/16 429/199 |
| 2003/0091905 A1 | | 5/2003 | Nobuta et al. | | |
| 2005/0219797 A1 | | 10/2005 | Nakamura et al. | | |

FOREIGN PATENT DOCUMENTS

| | | | |
|---|---|---|---|
| CN | 102842699 A | | 12/2012 |
| CN | 103258655 A | | 8/2013 |
| CN | 103730263 | * | 4/2014 |
| EP | 2 667 445 A1 | | 11/2013 |
| JP | 2003-123834 A | | 4/2003 |
| JP | 2006-202646 A | | 8/2006 |
| JP | 2007-184460 A | | 7/2007 |
| JP | 4858107 B2 | | 1/2012 |
| JP | 2012-109539 | * | 6/2012 |
| JP | 2012-109539 | | 6/2012 |
| KR | 10-2011-0080913 A | | 7/2011 |
| WO | 2009/015253 A2 | | 1/2009 |
| WO | WO 2009/015253 | * | 1/2009 |
| WO | 2011/083974 A2 | | 7/2011 |

OTHER PUBLICATIONS

Communication dated Mar. 26, 2018, from European Patent Office in counterpart application No. 15855531.8.
International Preliminary Report on Patentability with translation of Written Opinion dated May 2, 2017, issued by the International Searching Authority in application No. PCT/JP2015/079866.
International Search Report of PCT/JP2015/079866 dated Dec. 8, 2015 [PCT/ISA/210].

* cited by examiner

*Primary Examiner* — C Melissa Koslow
(74) *Attorney, Agent, or Firm* — Sughrue Mion, PLLC

(57) ABSTRACT

The present invention aims to provide an electrolyte solution containing a quaternary ammonium salt as an electrolyte salt and is capable of providing an electrochemical device having a high capacitance retention and reducing generation of gas. The electrolyte solution of the present invention contains a solvent, a quaternary ammonium salt, and a nitrogen-containing unsaturated cyclic compound. The unsaturated cyclic compound is a nitrogen-containing unsaturated heterocyclic compound. The unsaturated cyclic compound excludes salts of the unsaturated cyclic compound and ionic liquids obtainable from the unsaturated cyclic compound.

7 Claims, No Drawings

ELECTROLYTE SOLUTION AND ELECTROCHEMICAL DEVICE

CROSS REFERENCE TO RELATED APPLICATIONS

This application is a National Stage of International Application No. PCT/JP2015/079866, filed Oct. 22, 2015, claiming priority based on Japanese Patent Application No. 2014-221683, filed Oct. 30, 2014, the contents of all of which are incorporated herein by reference in their entirety.

BACKGROUND ART

In order to improve the characteristics of electric devices such as electric double-layer capacitors, methods of adding an additive to an electrolyte solution have been studied.

For example, in order to provide an electrolyte solution for electric double-layer capacitors having a low viscosity, a high electrical conductivity, a wide potential window, and excellent electrochemical stability, Patent Literature 1 proposes addition of a succinimide derivative having a specific structure to an electrolyte solution containing a quaternary ammonium salt as an electrolyte in a solvent.

CITATION LIST

Patent Literature

Patent Literature 1: JP 2007-184460 A

SUMMARY OF INVENTION

Technical Problem

Electrolyte solutions to be used in electric devices such as electric double-layer capacitors need to have not only an ability to retain the capacitance of an electrochemical device but also an ability to reduce generation of gas. If any gas is generated inside an electrochemical device, the gas increases the internal pressure. This may lead to peeling of components such as a separator and an electrode, possibly causing an increase in internal resistance and, in some cases, breakage of the electrochemical device. In the case of using a quaternary ammonium salt as an electrolyte salt, however, it was found that the capacitance retention needs to be improved and gas generation need to be more reduced.

In consideration of the above state of the art, the present invention aims to provide an electrolyte solution containing a quaternary ammonium salt as an electrolyte salt and is capable of providing an electrochemical device having a high capacitance retention and reducing generation of gas. Also, in consideration of the above state of the art, the present invention aims to provide an electrochemical device, such as an electric double-layer capacitor, having a high capacitance retention and reducing generation of gas.

Solution to Problem

The inventors found that the above problems can be solved by adding a nitrogen-containing unsaturated cyclic compound to an electrolyte solution, thereby completing the present invention.

In other words, the present invention relates to an electrolyte solution containing a solvent, a quaternary ammonium salt, and a nitrogen-containing unsaturated cyclic compound, the unsaturated cyclic compound being a nitrogen-containing unsaturated heterocyclic compound.

It should be noted that the unsaturated cyclic compound excludes salts of the unsaturated cyclic compound and ionic liquids obtainable from the unsaturated cyclic compound.

The unsaturated cyclic compound preferably accounts for 0.0005 to 5 mass % relative to the electrolyte solution.

The solvent preferably contains a compound containing a sulfonyl group, a sulfinyl group, a sultone group, a sulfate group, or a sulfite group.

The quaternary ammonium salt is preferably triethylmethylammonium tetrafluoroborate, tetraethylammonium tetrafluoroborate, or spirobipyrrolidinium tetrafluoroborate.

The unsaturated cyclic compound is preferably at least one selected from the group consisting of pyrrole, pyridine, azirine, azepine, imidazole, pyrazole, oxazole, thiazole, imidazoline, pyrazine, thiazine, and indole, and any of these compounds containing a substituent.

The electrolyte solution of the present invention is preferably intended to be used for an electrochemical device.

The electrolyte solution of the present invention is preferably intended to be used for an electric double-layer capacitor.

The present invention also relates to an electrochemical device including the electrolyte solution, a positive electrode, and a negative electrode.

The electrochemical device of the present invention is preferably an electric double-layer capacitor.

Advantageous Effects of Invention

Since the electrolyte solution of the present invention has the aforementioned configuration, it can provide an electrochemical device having a high capacitance retention and reducing generation of gas. The electrochemical device and electric double-layer capacitor of the present invention have a high capacitance retention and reduce generation gas.

DESCRIPTION OF EMBODIMENTS

The present invention will be specifically described hereinbelow.

The electrolyte solution of the present invention contains, in addition to a quaternary ammonium salt, a nitrogen-containing unsaturated cyclic compound as an additive.

The nitrogen-containing unsaturated cyclic compound is preferably a nitrogen-containing unsaturated heterocyclic compound.

The nitrogen-containing unsaturated cyclic compound is also preferably a cyclic compound containing a nitrogen atom in a ring and, in the same ring, an unsaturated bond among the bonds constituting the ring.

The nitrogen-containing unsaturated cyclic compound is more preferably a 3- to 7-membered nitrogen-containing aromatic heterocyclic compound, still more preferably a 5- or 6-membered nitrogen-containing aromatic heterocyclic compound.

The nitrogen-containing unsaturated cyclic compound includes compounds capable of forming a salt resulting from a reaction with an acid. However, the simple terms "unsaturated cyclic compound" and "nitrogen-containing aromatic heterocyclic compound" herein literally mean the respective compounds themselves, and exclude salts of the compounds and ionic liquids obtainable from the compounds.

The nitrogen-containing unsaturated cyclic compound preferably has a pKa value of 0.1 or higher. The pKa value is more preferably 0.2 or higher. The pKa of the unsaturated cyclic compound can be calculated from the basicity determined by potentiometry.

The nitrogen-containing unsaturated cyclic compound is preferably at least one selected from the group consisting of pyrrole, pyridine, azirine, azepine, imidazole, pyrazole, oxazole, thiazole, imidazoline, pyrazine, thiazine, and indole, and any of these compounds containing a substituent.

The nitrogen-containing unsaturated cyclic compound is also preferably at least one selected from the group consisting of pyrrole, pyridine, azirine rings, azepine rings, imidazole rings, pyrazole rings, oxazole, thiazole, imidazoline rings, pyrazine, thiazine rings, and indole, and any of these compounds containing a substituent.

It is more preferably at least one selected from the group consisting of pyrrole and pyridine, and any of these compounds containing a substituent.

The compound containing a substituent herein means a compound obtainable from thiazine, for example, by replacing a hydrogen atom bonding to a carbon atom or a nitrogen atom by a substituent.

Examples of the substituent include C1-C5 alkyl groups.

Examples of the compound containing a substituent also include compounds having a structure in which a nitrogen-containing unsaturated cyclic compound containing no substituent (e.g., pyrrole or pyridine) and a nitrogen-free cyclic compound (e.g., benzene) are bonded to each other while sharing a side. Mention may also be made to compounds having a structure in which nitrogen-containing unsaturated cyclic compounds containing no substituent (e.g., pyrrole and pyridine) are condensed while sharing a side. These compounds may further contain a substituent such as an alkyl group.

Examples of such compounds include benzothiazole, quinoline, quinoxaline, cinnoline, pteridine, and purine.

The nitrogen-containing unsaturated cyclic compound is still more preferably at least one selected from the group consisting of pyridine, methylpyridine, dibutylpyridine, pyrrole, pyrazole, oxazole, thiazole, benzothiazole, and pyrazine.

The nitrogen-containing unsaturated cyclic compound preferably accounts for 0.0005 to 5 mass %, more preferably 0.0010 mass % or more, still more preferably 0.0015 mass % or more, particularly preferably 0.01 mass % or more, while more preferably 4 mass % or less, still more preferably 3 mass % or less, particularly preferably 1 mass % or less, relative to the electrolyte solution.

Too small an amount of the nitrogen-containing unsaturated cyclic compound may fail to induce a high capacitance retention and generate gas easily. Too large an amount thereof may not only fail to induce the effects corresponding to the amount, but also impair the abilities that the electrochemical device originally needs to have.

The nitrogen-containing unsaturated cyclic compound is preferably different from one which is generally used as a quaternary ammonium salt.

The electrolyte solution of the present invention further contains a solvent. In the present invention, the solvent does not contain the aforementioned nitrogen-containing unsaturated cyclic compound.

The solvent preferably contains a sultone, a compound containing a sulfonyl group (—S(=O)$_2$—), a compound containing a sulfinyl group (—S(=O)—), a compound containing a sulfate group (—S(=O)$_2$(—O)—)$_2$), or a compound containing a sulfite group (—S(=O) (=O)—)$_2$), more preferably contains a compound containing a sulfonyl group, a sultone group, or a sulfate group.

The compound containing a sulfonyl group (—S(=O)$_2$—), a sulfinyl group (—S(=O)—), or a sulfate group (—S(=O)$_2$(—O)—)$_2$) is preferably at least one selected from the group consisting of sulfolane compounds, sultone compounds, and sulfate derivatives, more preferably a sulfolane compound.

The sulfolane compound may be a fluorine-free sulfolane compound or may be a fluorine-containing sulfolane compound.

Examples of the fluorine-free sulfolane compound include sulfolane, as well as fluorine-free sulfolane derivatives represented by the following formula:

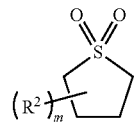

wherein $R^2$ is a C1-C4 alkyl group; and m is an integer of 1 or 2.

Preferred among these are the following sulfolane and sulfolane derivatives.

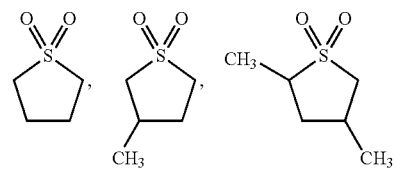

Examples of the fluorine-containing sulfolane compound include fluorine-containing sulfolane compounds disclosed in JP 2003-132944 A. In particular, those represented by the following formulas:

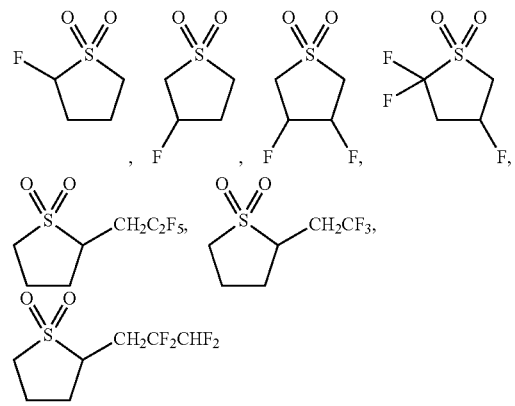

are preferred.

Preferred among these as the sulfolane compound are sulfolane, 3-methylsulfolane, and 2,4-dimethylsulfolane, and particularly preferred is sulfolane.

Examples of the sultone compounds include 1,3-propanesultone, 1-fluoro-1,3-propanesultone, 2-fluoro-1,3-propanesultone, 3-fluoro-1,3-propanesultone, 1-propene-1,3-sultone, 1-fluoro-1-propene-1,3-sultone, 2-fluoro-1-propene-1,3-sultone, 3-fluoro-1-propene-1,3-sultone, 1,4-butanesultone, 1-butene-1,4-sultone, and 3-butene-1,4-sultone. Preferred are 1,3-propanesultone and 1-propene-1,3-sultone.

Examples of the sulfate derivatives include 1,3,2-dioxathiolane-2,2-dioxide, 4-methyl-1,3,2-dioxathiolane-2,2-dioxide, and 4-ethyl-1,3,2-dioxathiolane-2,2-dioxide. Preferred among these is 1,3,2-dioxathiolane-2,2-dioxide.

The proportion of the compound containing a sulfonyl group, a sulfinyl group, or a sulfate group is more preferably 0.1 to 50 vol %, more preferably 0.5 vol % or more, still more preferably 1 vol % or more, while more preferably 25 vol % or less, still more preferably 15 vol % or less, particularly preferably 10 vol % or less, in the solvent constituting the electrolyte solution.

Too small an amount of the compound containing a sulfonyl group, a sulfinyl group, or a sulfate group may fail to induce a high capacitance retention and generate gas easily. Too large an amount thereof may not only fail to induce the effects corresponding to the amount, but also impair the abilities that the electrochemical device originally needs to have.

The solvent preferably further contains a nitrile compound.

Examples of the nitrile compound include nitrile compounds represented by the following formula (I):

$$R^1-(CN)_n \quad (I)$$

wherein $R^1$ is a C1-C10 alkyl group or a C1-C10 alkylene group; and n is an integer of 1 or 2.

In the formula (I), $R^1$ is a C1-C10 alkyl group when n is 1, and $R^1$ is a C1-C10 alkylene group when n is 2.

Examples of the alkyl group include C1-C10 alkyl groups such as a methyl group, an ethyl group, a propyl group, an isopropyl group, a butyl group, an isobutyl group, a tert-butyl group, a pentyl group, a neopentyl group, a hexyl group, a heptyl group, an octyl group, a nonyl group, and a decyl group. Preferred among these are a methyl group and an ethyl group.

Examples of the alkylene group include C1-C10 alkylene groups such as a methylene group, an ethylene group, a propylene group, a butylene group, a pentylene group, a hexylene group, an octylene group, a nonylene group, and a decylene group. Preferred are a propylene group and an ethylene group.

Specific examples of the nitrile compound include acetonitrile ($CH_3$—CN), propionitrile ($CH_3$—$CH_2$—CN), and glutaronitrile (NC—$(CH_2)_3$—CN). In order to achieve a low resistance, acetonitrile and propionitrile are preferred, and acetonitrile is particularly preferred.

The proportion of the nitrile compound is preferably 50 to 100 vol %, more preferably 75 vol % or more, still more preferably 85 vol % or more, further more preferably 90 vol % or more, particularly preferably 95 vol % or more, while more preferably 99.5 vol % or less, still more preferably 99 vol % or less, in the solvent constituting the electrolyte solution.

The electrolyte solution of the present invention further contains a quaternary ammonium salt.

Examples of the quaternary ammonium salt include the following.

(IIA) Tetraalkyl Quaternary Ammonium Salts

Preferred examples thereof include tetraalkyl quaternary ammonium salts represented by the following formula (IIA):

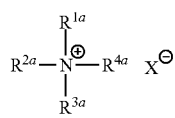

(wherein $R^{1a}$, $R^{2a}$, $R^{3a}$, and $R^{4a}$ may be the same as or different from each other and are each a C1-C6 alkyl group which may optionally contain an ether bond; and $X^-$ is an anion). In order to improve the oxidation resistance, salts derived from these ammonium salts are also preferred in which part or all of the hydrogen atoms therein is/are replaced by a fluorine atom(s) and/or a C1-C4 fluorine-containing alkyl group(s).

Specific examples thereof include:
tetraalkyl quaternary ammonium salts represented by the following formula (IIA-1):

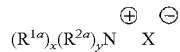

(wherein $R^{1a}$, $R^{2a}$, and $X^-$ are each defined as in the formula (IIA); and x and y may be the same as or different from each other and are each an integer of 0 to 4, and satisfy x+y=4); and alkyl ether group-containing trialkyl ammonium salts represented by the following formula (IIA-2):

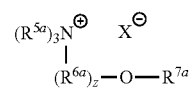

wherein $R^{5a}$ is a C1-C6 alkyl group; $R^{6a}$ is a C1-C6 divalent hydrocarbon group; $R^{7a}$ is a C1-C4 alkyl group; z is 1 or 2; and $X^-$ is an anion. Introduction of an alkyl ether group leads to viscosity reduction.

The anion $X^-$ may be an inorganic anion or may be an organic anion. Examples of the inorganic anion include $AlCl_4^-$, $BF_4^-$, $PF_6^-$, $AsF_6^-$, $TaF_6^-$, $I^-$, $SbF_6^-$ and $ClO_4^-$. Examples of the organic anion include $CF_3COO^-$, $CF_3SO_3^-$, $(CF_3SO_2)_2N^-$, $(C_2F_5SO_2)_2N^-$, and $C_4F_9SO_3^-$.

In order to achieve good oxidation resistance and ionic dissociation, $BF_4^-$, $PF_6^-$, $AsF_6^-$, and $SbF_6^-$ are preferred.

Specific, preferred examples of the tetraalkyl quaternary ammonium salts include $Et_4NBF_4$, $Et_4NClO_4$, $Et_4NPF_6$, $Et_4NAsF_6$, $Et_4NSbF_6$, $Et_4NCF_3SO_3$, $Et_4N(CF_3SO_2)_2N$, $Et_4NC_4F_9SO_3$, $Et_3MeNBF_4$, $Et_3MeNClO_4$, $Et_3MeNPF_6$, $Et_3MeNAsF_6$, $Et_3MeNSbF_6$, $Et_3MeNCF_3SO_3$, $Et_3MeN(CF_3SO_2)_2N$, $Et_3MeNC_4F_9SO_3$, and an N,N-diethyl-N-methyl-N-(2-methoxyethyl)ammonium salt. Particularly preferred are $Et_4NBF_4$, $Et_4NPF_6$, $Et_4NSbF_6$, $Et_4NAsF_6$, $Et_3MeNBF_4$, and an N,N-diethyl-N-methyl-N-(2-methoxyethyl)ammonium salt.

(IIB) Spirobipiperidinium Salts, spirobipyrrolidinium Salts, and piperidine-1-Spiro-1'-pyrrolidinium Salts Preferred examples thereof include spirobipiperidinium salts represented by the following formula (IIb-1):

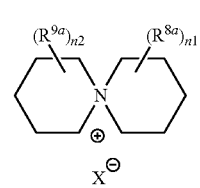

(wherein $R^{8a}$ and $R^{9a}$ may be the same as or different from each other and are each a C1-C4 alkyl group; $X^-$ is an anion; n1 is an integer of 0 to 5; and n2 is an integer of 0 to 5); piperidine-1-spiro-1'-pyrrolidinium salts represented by the following formula (IIb-2):

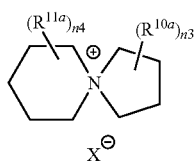

(IIb-2)

(wherein $R^{10a}$ and $R^{11a}$ may be the same as or different from each other and are each a C1-C4 alkyl group; $X^-$ is an anion; n3 is an integer of 0 to 5; and n4 is an integer of 0 to 5); and spirobipyrrolidinium salts represented by the following formula (IIb-3):

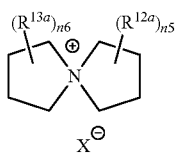

(IIb-3)

(wherein $R^{12a}$ and $R^{13a}$ may be the same as or different from each other and are each a C1-C4 alkyl group; $X^-$ is an anion; n5 is an integer of 0 to 5; and n6 is an integer of 0 to 5). In order to improve the oxidation resistance, salts derived from these salts are also preferred in which part or all of the hydrogen atoms therein is/are replaced by a fluorine atom(s) and/or a C1-C4 fluorine-containing alkyl group(s).

Specific, preferred examples of the anion $X^-$ include the same as those for the salts (IIA).

For example, those represented by the following formulas:

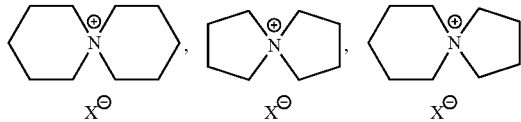

may be mentioned as specific, preferred examples.

These salts have excellent solubility, oxidation resistance, and ion conductivity.

(IIC) Imidazolium Salts

Preferred examples of the imidazolium salts include imidazolium salts represented by the following formula (IIC):

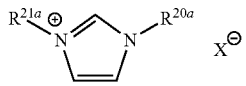

(wherein $R^{20a}$ and $R^{21a}$ may be the same as or different from each other and are each a C1-C6 alkyl group; and $X^-$ is an anion). In order to improve the oxidation resistance, salts derived from these imidazolium salts are also preferred in which part or all of the hydrogen atoms therein is/are replaced by a fluorine atom(s) and/or a C1-C4 fluorine-containing alkyl group(s).

Specific, preferred examples of the anion $X^-$ include the same as those mentioned for the salts (IIA).

For example, one represented by the following formula:

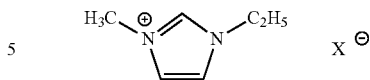

may be mentioned as a specific, preferred example.

This imidazolium salt is excellent in that it has a low viscosity and good solubility.

(IID) N-alkylpyridinium Salts

Preferred examples thereof include N-alkylpyridinium salts represented by the following formula (IID):

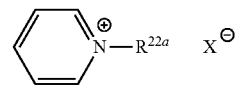

(wherein $R^{22a}$ is a C1-C6 alkyl group; and $X^-$ is an anion). In order to improve the oxidation resistance, salts derived from these N-alkylpyridinium salts are also preferred in which part or all of the hydrogen atoms therein is/are replaced by a fluorine atom(s) and/or a C1-C4 fluorine-containing alkyl group(s).

Specific, preferred examples of the anion $X^-$ include the same as those mentioned for the salts (IIA).

For example, those represented by the following formulas:

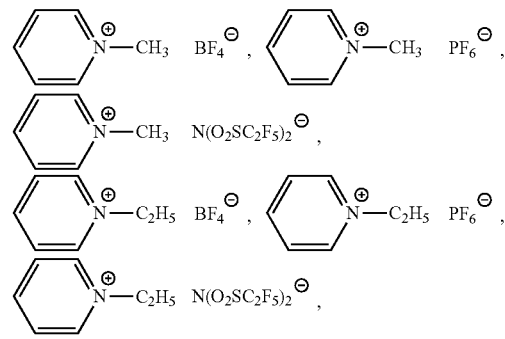

may be mentioned as specific, preferred examples.

These N-alkylpyridinium salts are excellent in that they have a low viscosity and good solubility.

(IIE) N,N-dialkylpyrrolidinium Salts

Preferred examples thereof include N,N-dialkylpyrrolidinium salts represented by the following formula (IIE):

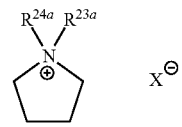

(wherein $R^{23a}$ and $R^{24a}$ may be the same as or different from each other and are each a C1-C6 alkyl group which may optionally have an ether bond; and $X^-$ represents an anion). In order to improve the oxidation resistance, salts derived from these N,N-dialkylpyrrolidinium salts are also preferred in which part or all of the hydrogen atoms therein is/are replaced by a fluorine atom(s) and/or a C1-C4 fluorine-containing alkyl group(s).

Specific, preferred examples of the anion X⁻ include the same as those mentioned for the salts (IIA).

For example, those represented by the following formulas:

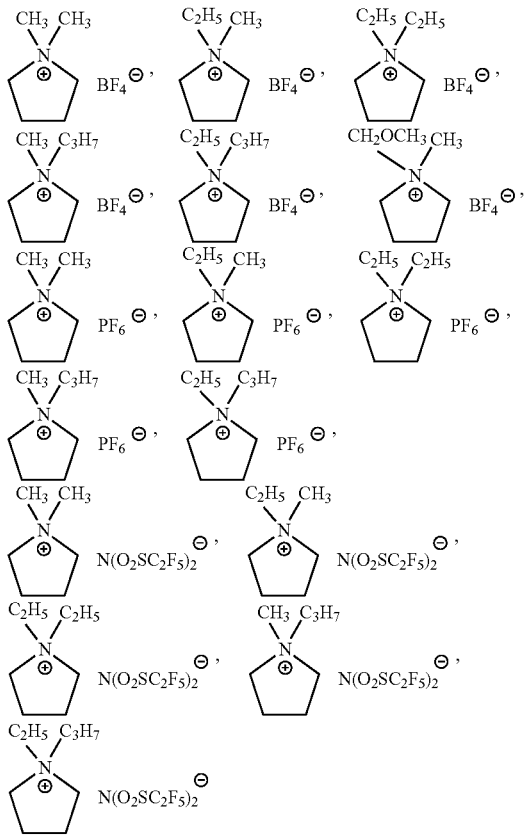

may be mentioned as specific, preferred examples.

These N,N-dialkylpyrrolidinium salts are excellent in that they have a low viscosity and good solubility.

The quaternary ammonium salt is preferably at least one selected from the group consisting of the salts (IIA), (IIB), (IIC), (IID), and (IIE), more preferably at least one selected from the group consisting of the salts (IIA), (IIB), (IID), and (IIE), still more preferably at least one selected from the group consisting of the salts (IIA) and (IIB) for good solubility, oxidation resistance, and ion conductivity, and further more preferably at least one selected from the group consisting of those represented by the following formulas:

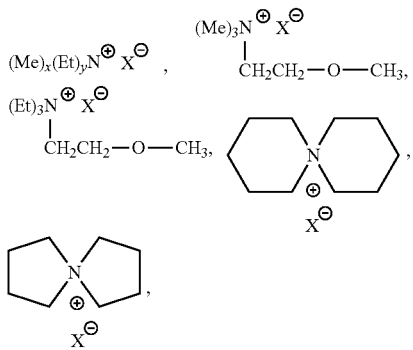

wherein Me represents a methyl group; Et represents an ethyl group; and X⁻, x, and y are the same as those mentioned in the formula (IIA-1).

The quaternary ammonium salt is preferably triethylmethylammonium tetrafluoroborate, tetraethylammonium tetrafluoroborate, or spirobipyrrolidinium tetrafluoroborate.

The concentration of the quaternary ammonium salt depends on factors such as the current density required, the use of the resulting product, and the type of the quaternary ammonium salt, and is preferably 0.1 to 2.5 mol/l. The concentration thereof is more preferably 0.5 mol/l or higher, still more preferably 0.7 mol/l or higher, while more preferably 2.0 mol/l or lower, still more preferably 0.9 mol/l or lower.

The electrolyte solution of the present invention may further contain another electrolyte salt in addition to the quaternary ammonium salt.

Such an additional electrolyte salt may be a lithium salt. Preferred examples of the lithium salt include $LiPF_6$, $LiBF_4$, $LiAsF_6$, $LiSbF_6$, and $LiN(SO_2C_2H_5)_2$.

In order to further improve the capacitance, a magnesium salt may be used. Preferred examples of the magnesium salt include $Mg(ClO_4)_2$ and $Mg(OOC_2H_5)_2$.

The solvent may further contain a fluorine-containing ether.

Examples of the fluorine-containing ether include a fluorine-containing acyclic ether (Ia) and a fluorine-containing cyclic ether (Ib).

Examples of the fluorine-containing acyclic ether (Ia) include the compounds disclosed in publications such as JP H08-37024 A, JP H09-97627 A, JP H11-26015 A, JP 2000-294281 A, JP 2001-52737 A, and JP H11-307123 A.

Preferred among these as the fluorine-containing acyclic ether (Ia) are fluorine-containing acyclic ethers represented by the following formula (Ia-1):

$$Rf^1{-}O{-}Rf^2 \qquad (Ia\text{-}1)$$

wherein $Rf^1$ is a C1-C10 fluoroalkyl group; and $Rf^2$ is a C1-C4 alkyl group which may optionally have a fluorine atom.

In the formula (Ia-1), $Rf^2$ is preferably a fluorine-containing alkyl group because such a structure, in comparison with the cases where $Rf^2$ is a fluorine-free alkyl group, leads to not only particularly better oxidation resistance and compatibility with an electrolyte salt, but also a higher decomposition voltage and a lower freezing point that enables maintenance of the low-temperature characteristics.

Examples of the group for $Rf^1$ include C1-C10 fluoroalkyl groups such as $HCF_2CF_2CH_2{-}$, $HCF_2CF_2CF_2CH_2{-}$, $HCF_2CF_2CF_2CF_2CH_2{-}$, $C_2F_5CH_2{-}$, $CF_3CFHCF_2CH_2{-}$, $HCF_2CF(CF_3)CH_2{-}$, $C_2F_5CH_2CH_2{-}$, and $CF_3CH_2CH_2{-}$. Preferred among these are C3-C6 fluoroalkyl groups.

Examples of the group for $Rf^2$ include C1-C4 fluorine-free alkyl groups, $-CF_2CF_2H$, $-CF_2CFHCF_3$, $-CF_2CF_2CF_2H$, $-CH_2CH_2CF_3$, $-CH_2CFHCF_3$, and $-CH_2CH_2C_2F_5$. Preferred among these are C2-C4 fluorine-containing alkyl groups.

Particularly preferably, in order to achieve good ion conductivity, $Rf^1$ is a C3-C4 fluorine-containing alkyl group and $Rf^2$ is a C2-C3 fluorine-containing alkyl group.

Specifically, for example, the fluorine-containing acyclic ether (Ia) may be one or two or more of $HCF_2CF_2CH_2OCF_2CF_2H$, $CF_3CF_2CH_2OCF_2CF_2H$, $HCF_2CF_2CH_2OCF_2CFHCF_3$, $CF_3CF_2CH_2OCF_2CFHCF_3$, $HCF_2CF_2CH_2OCH_2CFHCF_3$, and $CF_3CF_2CH_2OCH_2CFHCF_3$. In order to achieve a high decomposition voltage and to maintain the low-temperature characteristics, particularly preferred among these are $HCF_2CF_2CH_2OCF_2CF_2H$, $HCF_2CF_2CH_2OCF_2CFHCF_3$, $CF_3CF_2CH_2OCF_2CFHCF_3$, and $CF_3CF_2CH_2OCF_2CF_2H$.

For the fluorine-containing cyclic ether (Ib), those represented by the following formulas:

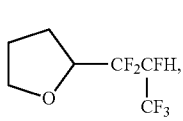 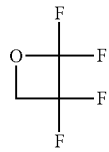

may be mentioned as examples thereof.

The solvent may further contain another solvent such as a cyclic carbonate (Ic) and an acyclic carbonate (Id).

The cyclic carbonate (Ic) may be a fluorine-free cyclic carbonate or may be a fluorine-containing cyclic carbonate.

Examples of the fluorine-free cyclic carbonate include ethylene carbonate (EC), propylene carbonate (PC), and vinylene carbonate. In order to reduce the internal resistance and to maintain the low-temperature characteristics, propylene carbonate (PC) is preferred.

Examples of the fluorine-containing cyclic carbonate include mono-, di-, tri-, or tetra-fluoroethylene carbonate and trifluoromethyl ethylene carbonate. In order to improve the withstand voltage of the resulting electrochemical device, trifluoromethyl ethylene carbonate is preferred.

The acyclic carbonate (Id) may be a fluorine-free acyclic carbonate or may be a fluorine-containing acyclic carbonate.

Examples of the fluorine-free acyclic carbonate include dimethyl carbonate (DMC), diethyl carbonate (DEC), ethyl methyl carbonate (EMC), methyl isopropyl carbonate (MIPC), ethyl isopropyl carbonate (EIPC), and 2,2,2-trifluoroethyl methyl carbonate (TFEMC). In order to reduce the internal resistance and to maintain the low-temperature characteristics, dimethyl carbonate (DMC) is preferred.

Examples of the fluorine-containing acyclic carbonate include:

fluorine-containing acyclic carbonates represented by the following formula (Id-1):

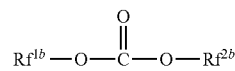

(wherein $Rf^{1a}$ is an alkyl group or a fluoroalkyl group containing an end group represented by the following formula:

$(HCX^{1a}X^{2a})\text{—}$ (wherein $X^{1a}$ and $X^{2a}$ may be the same as or different from each other and are each a hydrogen atom or a fluorine atom) and preferably having a fluorine content of 10 to 76 mass %, preferably a C1-C3 alkyl group; and $Rf^{2a}$ is a fluoroalkyl group containing an end group represented by the above formula or $CF_3$ and preferably having a fluorine content of 10 to 76 mass %);

fluorine-containing acyclic carbonates represented by the following formula (Id-2):

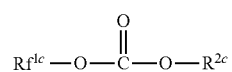

(wherein $Rf^{1b}$ is a fluorine-containing alkyl group containing an ether bond and a —$CF_3$ end group and having a fluorine content of 10 to 76 mass %; and $Rf^{2b}$ is a fluorine-containing alkyl group which may optionally contain an ether bond and which has a fluorine content of 10 to 76 mass %); and fluorine-containing acyclic carbonates represented by the following formula (Id-3):

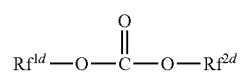

(wherein $Rf^{1c}$ is a fluorine-containing alkyl group containing an ether bond and an end group represented by $HCFX^{1c}$— (wherein $X^{1c}$ is a hydrogen atom or a fluorine atom) and having a fluorine content of 10 to 76 mass %; and $R^{2c}$ is an alkyl group in which a hydrogen atom may be replaced by a halogen atom and which may contain a hetero atom in the chain).

Specific examples of usable fluorine-containing acyclic carbonates include acyclic carbonates containing fluorine-containing groups in combination, represented by the following formula (Id-4):

$$Rf^{1d}\text{—}O\text{—}\overset{\overset{\displaystyle O}{\|}}{C}\text{—}O\text{—}Rf^{2d} \quad (\text{Id-4})$$

wherein $Rf^{1d}$ and $Rf^{2d}$ are each $H(CF_2)_2CH_2$—, $FCH_2CF_2CH_2$—, $H(CF_2)_2CH_2CH_2$—, $CF_3CF_2CH_2$—, $CF_3CH_2CH_2$—, $CF_3CF(CF_3)CH_2CH_2$—, $C_3F_7OCF(CF_3)CH_2$—, $CF_3OCF(CF_3)CH_2$—, $CF_3OCF_2$—, $CF_3CH_2$—, $CF_3$—, $(CF_3)_2CH$—, or the like.

In order to reduce the internal resistance and to maintain the low-temperature characteristics, the fluorine-containing acyclic carbonate is preferably any of the following.

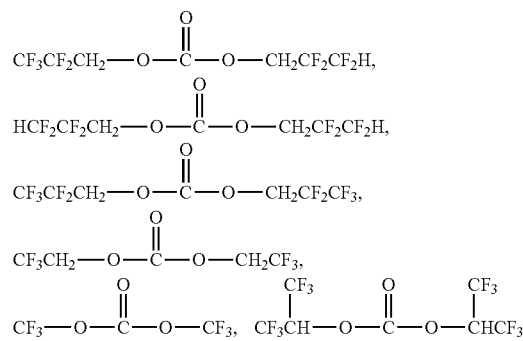

In addition, any of the following compounds may also be used as the fluorine-containing acyclic carbonate.

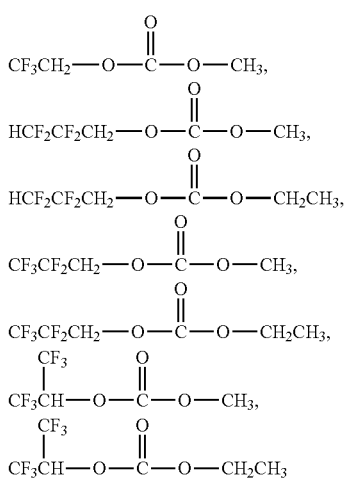

Examples of other solvents to be mixed different from the cyclic carbonate (Ic) and the acyclic carbonate (Id) include fluorine-free lactones and fluorine-containing lactones represented by the following formulas:

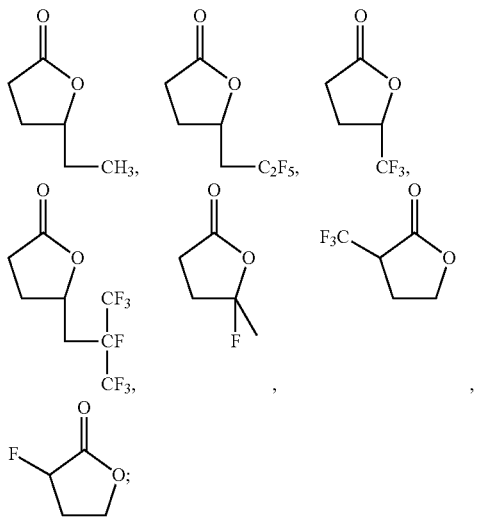

furans; and oxolanes.

Further, the electrolyte solution of the present invention may be a gel electrolyte solution gelled (plasticized) in combination with a polymer material.

Examples of such a polymer material include conventionally known polyethylene oxide and polypropylene oxide, and modified products thereof (JP H08-222270 A, JP 2002-100405 A); polyacrylate-based polymers, polyacrylonitrile, and fluororesins such as polyvinylidene fluoride and vinylidene fluoride-hexafluoropropylene copolymers (JP H04-506726 T, JP H08-507407 T, JP H10-294131 A); and complexes of any of these fluororesins and any hydrocarbon resin (JP H11-35765 A, JP H11-86630 A). In particular, polyvinylidene fluoride or a vinylidene fluoride-hexafluoropropylene copolymer is preferably used as the polymer material for a gel electrolyte solution.

In addition, any ion-conducting compound disclosed in JP 2006-114401 A may also be used.

Such an ion-conducting compound is an amorphous fluorine-containing polyether compound which contains a fluorine-containing group in a side chain and is represented by the following formula (1-1):

$$P\text{-}(D)\text{-}Q \tag{1-1}$$

wherein D is a unit represented by the following formula (2-1):

$$\text{-}(D1)_n\text{-}(FAE)_m\text{-}(AE)_p\text{-}(Y)_q\text{-} \tag{2-1}$$

wherein

D1 is an ether unit which contains a fluorine-containing organic group containing an ether bond in a side chain and which is represented by the following formula (2a):

(2a)

(wherein Rf is a fluorine-containing organic group which contains an ether bond and which may optionally contain a crosslinkable functional group; and $R^{15a}$ is a group or an atomic bond that couples Rf with the main chain);

FAE is an ether unit which contains a fluorine-containing alkyl group in a side chain and which is represented by the following formula (2b):

(2b)

(wherein Rfa is a hydrogen atom or a fluorine-containing alkyl group which may optionally contain a crosslinkable functional group; and $R^{16a}$ is a group or an atomic bond that couples Rfa with the main chain);

AE is an ether unit represented by the following formula (2c):

(2c)

(wherein $R^{18a}$ is a hydrogen atom, an alkyl group which may optionally contain a crosslinkable functional group, an alicyclic hydrocarbon group which may optionally contain a crosslinkable functional group, or an aromatic hydrocarbon group which may optionally contain a crosslinkable functional group; and $R^{17a}$ is a group or an atomic bond that couples $R^{18a}$ with the main chain);

Y is a unit containing at least one of the units represented by the following formulas (2d-1) to (2d-3),

(2d-1)

(2d-2)

-continued (2d-3)

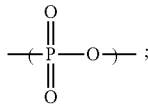

n is an integer of 0 to 200;
m is an integer of 0 to 200;
p is an integer of 0 to 10000; and
q is an integer of 1 to 100,
where n+m is not 0 and the order of bonding of D1, FAE, AE, and Y is not specified; and P and Q may be the same as or different from each other and are each a hydrogen atom, an alkyl group which may optionally contain a fluorine atom and/or a crosslinkable functional group, a phenyl group which may optionally contain a fluorine atom and/or a crosslinkable functional group, a —COOH group, —OR$^{19a}$ (where R$^{19a}$ is a hydrogen atom or an alkyl group which may optionally contain a fluorine atom and/or a crosslinkable functional group), an ester group, or a carbonate group (if a terminal of D is an oxygen atom, neither P nor Q is a —COOH group, —OR$^{19a}$, an ester group, and a carbonate group).

The electrolyte solution of the present invention may contain another additive, if needed. Examples of such an additive include metal oxides and glass. These may be used to the extent that the effects of the present invention are not impaired.

Preferably, the electrolyte solution of the present invention does not freeze or the electrolyte salt does not precipitate at low temperature (e.g., 0° C. or −20° C.). Specifically, the viscosity is preferably 100 mPa·s or lower, more preferably 30 mPa·s or lower, particularly preferably 15 mPa·s or lower, at 0° C. Further, specifically, the viscosity is preferably 100 mPa·s or lower, more preferably 40 mPa·s or lower, particularly preferably 15 mPa·s or lower, at −20° C.

The electrolyte solution of the present invention is preferably a nonaqueous electrolyte solution.

The electrolyte solution of the present invention is useful as an electrolyte solution of various electrochemical devices containing an electrolyte solution. Examples of the electrochemical devices include electric double-layer capacitors, lithium secondary batteries, radical batteries, solar cells (especially, dye sensitized solar cells), fuel cells, various electrochemical sensors, electrochromic elements, electrochemical switching elements, aluminum electrolytic capacitors, and tantalum electrolytic capacitors. Preferred among these are electric double-layer capacitors and lithium secondary batteries, and particularly preferred are electric double-layer capacitors. Further, the electrolyte solution of the present invention is also usable as an ion conductor of antistatic coating materials, for example.

As mentioned above, the electrolyte solution of the present invention is preferably intended to be used for electrochemical devices, particularly preferably for electric double-layer capacitors.

An electrochemical device including the electrolyte solution of the present invention, a positive electrode, and a negative electrode is also one aspect of the present invention. Examples of the electrochemical device include those mentioned above, and an electric double-layer capacitor is particularly preferred.

The following will describe in detail a case where the electrochemical device of the present invention is an electric double-layer capacitor.

In the electric double-layer capacitor of the present invention, one or both of the positive electrode and the negative electrode is/are preferably a polarizable electrode. The polarizable electrode and a non-polarizable electrode may be the following electrodes specifically disclosed in JP H09-7896 A.

The polarizable electrode may be a polarizable electrode mainly containing activated carbon, and it preferably contains inactive carbon having a large specific surface area and a conducting agent (e.g., carbon black) which imparts electronic conductivity. The polarizable electrode can be formed by various methods. For example, a polarizable electrode containing activated carbon and carbon black can be formed by mixing activated carbon powder, carbon black, and a phenolic resin, press-molding the mixture, and then firing and activating the mixture in an inert gas atmosphere and in a steam atmosphere. This polarizable electrode is preferably bonded to a current collector using, for example, a conductive adhesive.

Alternatively, a polarizable electrode may be formed by kneading activated carbon powder, carbon black, and a binder in the presence of an alcohol to form a sheet-like mixture, and then drying the sheet-like mixture. This binder may be polytetrafluoroethylene, for example. Alternatively, a polarizable electrode integrated with a current collector may be formed by mixing activated carbon powder, carbon black, a binder, and a solvent to form slurry, applying this slurry to a metal foil of a current collector, and drying the applied slurry.

Both electrodes of the electric double-layer capacitor may be polarizable electrodes mainly containing activated carbon. Alternatively, the electric double-layer capacitor may have a structure in which one electrode thereof is a non-polarizable electrode. Examples of such a structure include a combination of a positive electrode mainly containing a cell active material such as a metal oxide and a negative electrode which is a polarizable electrode mainly containing activated carbon; and a combination of a negative electrode of metallic lithium or a lithium alloy and a polarizable electrode mainly containing activated carbon.

In place of or in combination with activated carbon, a carbonaceous material may be used such as carbon black, graphite, expanded graphite, porous carbon, carbon nanotube, carbon nanohorn, and ketjen black.

The solvent to be used for preparation of slurry in the production of an electrode is preferably one that dissolves a binder. The solvent is appropriately selected from N-methylpyrrolidone, dimethylformamide, toluene, xylene, isophorone, methyl ethyl ketone, ethyl acetate, methyl acetate, dimethyl phthalate, ethanol, methanol, butanol, and water in accordance with the type of the binder.

Examples of the activated carbon to be used for a polarizable electrode include phenol resin-based activated carbon, coconut shell-based activated carbon, and petroleum coke-based activated carbon. In order to achieve a large capacitance, petroleum coke-based activated carbon or phenol resin-based activated carbon is preferred. Further, examples of an activation method to prepare activated carbon include steam activation and molten KOH activation. In order to achieve a larger capacitance, the use of activated carbon obtainable by the molten KOH activation is preferred.

Preferred examples of the conducting agent to be used for a polarizable electrode include carbon black, ketjen black, acetylene black, natural graphite, artificial graphite, metal fibers, conductive titanium oxide, and ruthenium oxide. In order to achieve good conductivity (low internal resistance), and since too large an amount of the conducting agent may lower the capacitance of a product, the amount of the conducting agent (e.g., carbon black) to be used for a polarizable electrode is preferably 1 to 50 mass % in the sum of the amounts of the conducting agent and the activated carbon.

In order to provide an electric double-layer capacitor having a large capacitance and a low internal resistance, the activated carbon to be used for a polarizable electrode is preferably activated carbon having an average particle size of 20 μm or smaller and a specific surface area of 1500 to 3000 m$^2$/g.

The current collector may be any one which is chemically and electrochemically resistant to corrosion. Preferred examples of the current collector of a polarizable electrode mainly containing activated carbon include stainless steel, aluminum, titanium, and tantalum. Aluminum is a particularly preferred material among these in terms of both the characteristics and cost of the resulting electric double-layer capacitor.

Examples of commonly known electric double-layer capacitors include wound-type electric double-layer capacitors, laminate-type electric double-layer capacitors, and coin-type electric double-layer capacitors. The electric double-layer capacitor of the present invention may be of any of these types.

For example, a wound-type electric double-layer capacitor may be produced by winding a positive electrode and a negative electrode each having a laminate (electrode) of a current collector and an electrode layer with a separator in between to form a wound element, putting this wound element into a container made of, for example, aluminum, filling the container with an electrolyte solution, and then sealing the container with a rubber sealing material.

The separator may be formed from any conventionally known material and may have any conventionally known structure in the present invention. Examples thereof include a polyethylene porous membrane and nonwoven fabric of polypropylene fibers, glass fibers, or cellulose fibers.

Alternatively, by a known method, an electric double-layer capacitor may be prepared in the form of a laminate-type electric double-layer capacitor including sheet-like positive and negative electrodes stacked with each other with an electrolyte solution and a separator in between, or in the form of a coin-type electric double-layer capacitor including a positive electrode and a negative electrode fixed in a coin shape using a gasket with an electrolyte solution and a separator in between.

Even if the electrochemical device of the present invention is a device different from electric double-layer capacitors, it may have any configuration as long as the electrolyte solution used therein is the electrolyte solution of the present invention. For example, a conventionally known configuration may be used.

EXAMPLES

The following will describe the present invention referring to, but not limited to, examples.

The nitrogen-containing unsaturated cyclic compounds used in the examples are as follows.
(Nitrogen-Containing Unsaturated Cyclic Compounds)
  2,6-Di-tert-butylpyridine
  Pyridine (pKa=5.3)
  2-Methylpyridine (pKa=5.3)
  Pyrrole (pKa=0.4)
  Pyrazole
  Benzothiazole

Example 1

Acetonitrile and sulfolane were mixed at a ratio as shown in Table 1, whereby a solvent was prepared. Then, 2,6-di-tert-butylpyridine was added thereto such that the amount thereof was 0.0005 mass % relative to the resulting electrolyte solution, and spirobipyrrolidinium tetrafluoroborate (SBPBF4) was added thereto such that the concentration thereof was 0.8 mol/L (0.8M), whereby an electrolyte solution was prepared.

Using the resulting electrolyte solution, a laminate cell electric double-layer capacitor was produced by the following method. The resulting laminate cell electric double-layer capacitor was evaluated for the capacitance retention and the amount of gas generated. Table 1 shows the results.
(Production of Electrode)
(Preparation of Slurry for Electrodes)

First, 100 parts by weight of coconut shell activated carbon activated by steam (YP5OF, Kuraray Chemical Co., Ltd.), 3 parts by weight of acetylene black (DENKA BLACK, Denki Kagaku Kogyo K.K.) as a conductive agent, 2 parts by weight of ketjen black (carbon ECP600JD, Lion Corp.), 4 parts by weight of elastomer binder, 2 parts by weight of PTFE (POLYFLON PTFE D-210C, Daikin Industries, Ltd.), and a surfactant (trade name: DN-800H, Daicel Corp.) were mixed to provide slurry for electrodes.

Edged aluminums (20CB, Japan Capacitor Industrial Co., Ltd.) were prepared as current collectors. To one face of each current collector was applied the slurry for electrodes using a coating device, and thus electrode layers (thickness: 100 μm) were formed. Thereby, electrodes were produced.
(Production of Laminate Cell Electric Double-Layer Capacitor)

The electrodes were cut into a predetermined size (20×72 mm). Electrode leads were welded to the aluminum surfaces of the respective current collectors, and a separator (TF45-30, Nippon Kodoshi Corp.) was inserted between the electrodes. The workpiece was put into a laminate case (product No. D-EL40H, Dai Nippon Printing Co., Ltd.). An electrolyte solution was filled into the case and the workpiece was impregnated therewith in a dry chamber. Then, the case was sealed, whereby a laminate cell electric double-layer capacitor was produced.
<Capacitance Retention and Amount of Gas Generated>

The laminate cell electric double-layer capacitor was put into a thermostat chamber at a temperature of 65° C., and the capacitance and the amount of gas generated were measured by applying a voltage of 3.0 V for 500 hours. The measurement timings were initial (0 hours), 250 hours, and 500 hours. Based on the measured values, the capacitance retention (%) and the amount of gas generated (ml) were calculated by the following formulas:

Capacitance retention (%)=(capacitance at each timing/capacitance before evaluation (initial))×100; and Amount of gas generated (ml)=(volume of laminate cell at each timing)−(volume of laminate cell before evaluation (initial)).

Examples 2 to 60

An electrolyte solution was prepared in the same manner as in Example 1 except that a solvent was prepared and an additive and an electrolyte salt were added so as to achieve the proportions as shown in one of Tables 1 to 9 and 11. Further, a laminate cell electric double-layer capacitor was produced, and was measured for the capacitance retention and the amount of gas generated. Tables 1 to 9 and 11 show the results.

In preparation of the slurry for electrodes, Examples 2 to 54 used the same coconut shell activated carbon (YP50F, Kuraray Chemical Co., Ltd.) as in Example 1, while Examples 55 to 60 used YP80F (Kuraray Chemical Co., Ltd.) as coconut shell activated carbon.

The amounts of the additives in Tables 1 to 11 are each represented by the mass ratio of the additive to the electrolyte solution. "TEABF4" in Tables 1, 10, and 11 represents "tetraethylammonium tetrafluoroborate".

Comparative Examples 1 to 8

An electrolyte solution was prepared in the same manner as in Example 1 except that a solvent was prepared and an electrolyte salt was added so as to achieve the proportions as shown in Table 10. Further, a laminate cell electric double-layer capacitor was produced, and was measured for the capacitance retention and the amount of gas generated. Table 10 shows the results.

TABLE 1

|  |  | Example 1 | Example 2 | Example 3 | Example 4 | Example 5 |
|---|---|---|---|---|---|---|
| Salt | SBPBF4 | 0.8M | 0.8M | 0.8M | 0.8M | 0.8M |
|  | TEABF4 | 0 | 0 | 0 | 0 | 0 |
| Solvent | Acetonitrile (vol %) | 97.5% | 97.5% | 97.5% | 97.5% | 97.5% |
|  | Sulfolane (vol %) | 2.5% | 2.5% | 2.5% | 2.5% | 2.5% |
| Additive | 2,6-Di-tert-butylpyridine (mass %) | 0.0005 mass % | 0.05 mass % | 0.5 mass % | 0.75 mass % | 5.0 mass % |
|  | Amount of gas generated (ml) |  |  |  |  |  |
| Measurement results | 0 h | 0 | 0 | 0 | 0 | 0 |
|  | 250 h | 0.4 | 0.3 | 0.2 | 0.2 | 0.3 |
|  | 500 h | 0.8 | 0.7 | 0.5 | 0.5 | 0.7 |
|  | Initial performance (capacitance (F)) | 3.7 | 3.7 | 3.7 | 3.7 | 3.7 |
|  | Capacitance retention (%) |  |  |  |  |  |
|  | 0 h | 100 | 100 | 100 | 100 | 100 |
|  | 250 h | 94 | 95 | 95 | 95 | 95 |
|  | 500 h | 89 | 90 | 90 | 90 | 90 |

|  |  | Example 6 | Example 7 | Example 8 | Example 9 | Example 10 |
|---|---|---|---|---|---|---|
| Salt | SBPBF4 | 0.8M | 0 | 0 | 0 | 0 |
|  | TEABF4 | 0 | 0.8M | 0.8M | 0.8M | 0.8M |
| Solvent | Acetonitrile (vol %) | 97.5% | 97.5% | 97.5% | 97.5% | 97.5% |
|  | Sulfolane (vol %) | 2.5% | 2.5% | 2.5% | 2.5% | 2.5% |
| Additive | 2,6-Di-tert-butylpyridine (mass %) | 7.5 mass % | 0.05 mass % | 0.5 mass % | 0.75 mass % | 5.0 mass % |
|  | Amount of gas generated (ml) |  |  |  |  |  |
| Measurement results | 0 h | 0 | 0 | 0 | 0 | 0 |
|  | 250 h | 0.9 | 0.3 | 0.3 | 0.3 | 0.4 |
|  | 500 h | 1.8 | 0.7 | 0.6 | 0.6 | 0.8 |
|  | Initial performance (capacitance (F)) | 3.7 | 3.4 | 3.4 | 3.4 | 3.4 |
|  | Capacitance retention (%) |  |  |  |  |  |
|  | 0 h | 100 | 100 | 100 | 100 | 100 |
|  | 250 h | 90 | 86 | 86 | 86 | 85 |
|  | 500 h | 84 | 84 | 84 | 84 | 82 |

TABLE 2

|  |  | Example 11 | Example 12 | Example 13 | Example 14 | Example 15 | Example 16 |
|---|---|---|---|---|---|---|---|
| Salt | SBPBF4 | 0.8M | 0.8M | 0.8M | 0.8M | 0.8M | 0.8M |
| Solvent | Acetonitrile (vol %) | 97.5% | 97.5% | 97.5% | 97.5% | 97.5% | 97.5% |
|  | Sulfolane (vol %) | 2.5% | 2.5% | 2.5% | 2.5% | 2.5% | 2.5% |
| Additive | Pyridine | 0.0005 mass % | 0.05 mass % | 0.5 mass % | 0.75 mass % | 5.0 mass % | 7.5 mass % |
|  | Amount of gas generated (ml) |  |  |  |  |  |  |
| Measurement results | 0 h | 0 | 0 | 0 | 0 | 0 | 0 |
|  | 250 h | 0.2 | 0.2 | 0.1 | 0.1 | 0.2 | 0.6 |

TABLE 2-continued

|  |  |  |  |  |  |  |  |
|---|---|---|---|---|---|---|---|
|  | 500 h | 0.4 | 0.4 | 0.3 | 0.3 | 0.4 | 1.2 |
|  | Initial performance (capacitance (F)) | 3.7 | 3.7 | 3.7 | 3.7 | 3.7 | 3.7 |
|  | Capacitance retention (%) |  |  |  |  |  |  |
|  | 0 h | 100 | 100 | 100 | 100 | 100 | 100 |
|  | 250 h | 96 | 96 | 96 | 96 | 95 | 90 |
|  | 500 h | 91 | 92 | 92 | 92 | 91 | 85 |

|  |  | Example 17 | Example 18 | Example 19 | Example 20 | Example 21 | Example 22 |
|---|---|---|---|---|---|---|---|
| Salt | SBPBF4 | 0.8M | 0.8M | 0.8M | 0.8M | 0.9M | 0.7M |
| Solvent | Acetonitrile (vol %) | 95.0% | 95.0% | 95.0% | 95.0% | 97.5% | 97.5% |
|  | Sulfolane (vol %) | 5.0% | 5.0% | 5.0% | 5.0% | 2.5% | 2.5% |
| Additive | Pyridine | 0.05 mass % | 0.5 mass % | 0.75 mass % | 5.0 mass % | 0.5 mass % | 0.5 mass % |
|  | Amount of gas generated (ml) |  |  |  |  |  |  |
| Measurement results | 0 h | 0 | 0 | 0 | 0 | 0 | 0 |
|  | 250 h | 0.2 | 0.1 | 0.1 | 0.2 | 0.2 | 0.2 |
|  | 500 h | 0.4 | 0.3 | 0.3 | 0.4 | 0.5 | 0.4 |
|  | Initial performance (capacitance (F)) | 3.7 | 3.7 | 3.7 | 3.7 | 3.7 | 3.7 |
|  | Capacitance retention (%) |  |  |  |  |  |  |
|  | 0 h | 100 | 100 | 100 | 100 | 100 | 100 |
|  | 250 h | 96 | 96 | 96 | 95 | 95 | 95 |
|  | 500 h | 92 | 92 | 92 | 91 | 90 | 91 |

TABLE 3

|  |  | Example 23 | Example 24 | Example 25 | Example 26 |
|---|---|---|---|---|---|
| Salt | SBPBF4 | 0.8M | 0.8M | 0.8M | 0.8M |
| Solvent | Acetonitrile (vol %) | 100.0% | 100.0% | 100.0% | 100.0% |
|  | Sulfolane (vol %) | 0.0% | 0.0% | 0.0% | 0.0% |
| Additive | Pyridine | 0.05 mass % | 0.5 mass % | 0.75 mass % | 5.0 mass % |
| Measurement results | Amount of gas generated (ml) |  |  |  |  |
|  | 0 h | 0 | 0 | 0 | 0 |
|  | 250 h | 0.3 | 0.2 | 0.2 | 0.4 |
|  | 500 h | 0.7 | 0.5 | 0.5 | 0.8 |
|  | Initial performance (capacitance (F)) | 3.7 | 3.7 | 3.7 | 3.7 |
|  | Capacitance retention (%) |  |  |  |  |
|  | 0 h | 100 | 100 | 100 | 100 |
|  | 250 h | 94 | 94 | 94 | 94 |
|  | 500 h | 90 | 90 | 90 | 90 |

TABLE 4

|  |  | Example 27 | Example 28 | Example 29 | Example 30 | Example 31 | Example 32 | Example 33 | Example 34 |
|---|---|---|---|---|---|---|---|---|---|
| Salt | SBPBF4 | 0.8M | 0.8M | 0.8M | 0.8M | 0.8M | 0.8M | 0.8M | 0.8M |
| Solvent | Acetonitrile (vol %) | 97.5% | 97.5% | 97.5% | 97.5% | 95.0% | 95.0% | 95.0% | 95.0% |
|  | Sulfolane (vol %) | 2.5% | 2.5% | 2.5% | 2.5% | 5.0% | 5.0% | 5.0% | 5.0% |
| Additive | 2-Methylpyridine | 0.05 mass % | 0.5 mass % | 0.75 mass % | 5.0 mass % | 0.05 mass % | 0.5 mass % | 0.75 mass % | 5.0 mass % |
|  | Amount of gas generated (ml) |  |  |  |  |  |  |  |  |
| Measurement results | 0 h | 0 | 0 | 0 | 0 | 0 | 0 | 0 | 0 |
|  | 250 h | 0.3 | 0.2 | 0.2 | 0.4 | 0.3 | 0.2 | 0.2 | 0.4 |

TABLE 4-continued

|  | | Example 27 | Example 28 | Example 29 | Example 30 | Example 31 | Example 32 | Example 33 | Example 34 |
|---|---|---|---|---|---|---|---|---|---|
| | 500 h | 0.6 | 0.5 | 0.5 | 0.8 | 0.6 | 0.4 | 0.4 | 0.8 |
| | Initial performance (capacitance (F)) | 3.7 | 3.7 | 3.7 | 3.7 | 3.7 | 3.7 | 3.7 | 3.7 |
| | Capacitance retention (%) | | | | | | | | |
| | 0 h | 100 | 100 | 100 | 100 | 100 | 100 | 100 | 100 |
| | 250 h | 95 | 95 | 95 | 94 | 95 | 95 | 95 | 94 |
| | 500 h | 91 | 91 | 91 | 90 | 91 | 91 | 91 | 90 |

TABLE 5

| | | Example 35 | Example 36 | Example 37 | Example 38 |
|---|---|---|---|---|---|
| Salt | SBPBF4 | 0.8M | 0.8M | 0.8M | 0.8M |
| Solvent | Acetonitrile (vol %) | 97.5% | 97.5% | 97.5% | 97.5% |
| | Sulfolane (vol %) | 2.5% | 2.5% | 2.5% | 2.5% |
| Additive | Pyrrole | 0.05 mass % | 0.5 mass % | 0.75 mass % | 5.0 mass % |
| Measurement results | Amount of gas generated (ml) | | | | |
| | 0 h | 0 | 0 | 0 | 0 |
| | 250 h | 0.3 | 0.2 | 0.2 | 0.4 |
| | 500 h | 0.5 | 0.4 | 0.4 | 0.7 |
| | Initial performance (capacitance (F)) | 3.7 | 3.7 | 3.7 | 3.7 |
| | Capacitance retention (%) | | | | |
| | 0 h | 100 | 100 | 100 | 100 |
| | 250 h | 95 | 95 | 95 | 94 |
| | 500 h | 91 | 91 | 91 | 90 |

TABLE 6

| | | Example 39 | Example 40 | Example 41 | Example 42 |
|---|---|---|---|---|---|
| Salt | SBPBF4 | 0.8M | 0.8M | 0.8M | 0.8M |
| Solvent | Acetonitrile (vol %) | 97.5% | 97.5% | 97.5% | 97.5% |
| | 1,3 Propanesultone (vol %) | 2.5% | 2.5% | 2.5% | 2.5% |
| Additive | Pyridine | 0.05 mass % | 0.5 mass % | 0.75 mass % | 5.0 mass % |
| Measurement results | Amount of gas generated (ml) | | | | |
| | 0 h | 0 | 0 | 0 | 0 |
| | 250 h | 0.2 | 0.1 | 0.1 | 0.2 |
| | 500 h | 0.5 | 0.4 | 0.4 | 0.5 |
| | Initial performance (capacitance (F)) | 3.7 | 3.7 | 3.7 | 3.7 |
| | Capacitance retention (%) | | | | |
| | 0 h | 100 | 100 | 100 | 100 |
| | 250 h | 95 | 95 | 95 | 94 |
| | 500 h | 91 | 91 | 91 | 90 |

TABLE 7

| | | Example 43 | Example 44 | Example 45 | Example 46 |
|---|---|---|---|---|---|
| Salt | SBPBF4 | 0.8M | 0.8M | 0.8M | 0.8M |
| Solvent | Acetonitrile (vol %) | 97.5% | 97.5% | 97.5% | 97.5% |
| | 1,3,2-Dioxathiolane-2,2-dioxide (vol %) | 2.5% | 2.5% | 2.5% | 2.5% |
| Additive | Pyridine | 0.05 mass % | 0.5 mass % | 0.75 mass % | 5.0 mass % |
| Measurement results | Amount of gas generated (ml) | | | | |
| | 0 h | 0 | 0 | 0 | 0 |
| | 250 h | 0.3 | 0.2 | 0.2 | 0.3 |
| | 500 h | 0.6 | 0.5 | 0.5 | 0.6 |

TABLE 7-continued

|  | Example 43 | Example 44 | Example 45 | Example 46 |
|---|---|---|---|---|
| Initial performance (capacitance (F)) | 3.7 | 3.7 | 3.7 | 3.7 |
| Capacitance retention (%) | | | | |
| 0 h | 100 | 100 | 100 | 100 |
| 250 h | 94 | 94 | 94 | 94 |
| 500 h | 90 | 90 | 90 | 89 |

TABLE 8

|  |  | Example 47 | Example 48 | Example 49 | Example 50 |
|---|---|---|---|---|---|
| Salt | SBPBF4 | 0.8M | 0.8M | 0.8M | 0.8M |
| Solvent | Acetonitrile (vol %) | 97.5% | 97.5% | 97.5% | 97.5% |
|  | Sulfolane (vol %) | 2.5% | 2.5% | 2.5% | 2.5% |
| Additive | Pyrazole | 0.05 mass % | 0.5 mass % | 0.75 mass % | 5.0 mass % |
| Measurement results | Amount of gas generated (ml) | | | | |
|  | 0 h | 0 | 0 | 0 | 0 |
|  | 250 h | 0.2 | 0.1 | 0.1 | 0.2 |
|  | 500 h | 0.4 | 0.3 | 0.3 | 0.4 |
|  | Initial performance (capacitance (F)) | 3.7 | 3.7 | 3.7 | 3.7 |
|  | Capacitance retention (%) | | | | |
|  | 0 h | 100 | 100 | 100 | 100 |
|  | 250 h | 97 | 96 | 96 | 95 |
|  | 500 h | 93 | 92 | 92 | 93 |

TABLE 9

|  |  | Example 51 | Example 52 | Example 53 | Example 54 |
|---|---|---|---|---|---|
| Salt | SBPBF4 | 0.8M | 0.8M | 0.8M | 0.8M |
| Solvent | Acetonitrile (vol %) | 97.5% | 97.5% | 97.5% | 97.5% |
|  | Sulfolane (vol %) | 2.5% | 2.5% | 2.5% | 2.5% |
| Additive | Benzothiazole | 0.05 mass % | 0.5 mass % | 0.75 mass % | 5.0 mass % |
| Measurement results | Amount of gas generated (ml) | | | | |
|  | 0 h | 0 | 0 | 0 | 0 |
|  | 250 h | 0.2 | 0.1 | 0.1 | 0.2 |
|  | 500 h | 0.5 | 0.3 | 0.3 | 0.5 |
|  | Initial performance (capacitance (F)) | 3.7 | 3.7 | 3.7 | 3.7 |
|  | Capacitance retention (%) | | | | |
|  | 0 h | 100 | 100 | 100 | 100 |
|  | 250 h | 97 | 96 | 96 | 95 |
|  | 500 h | 92 | 92 | 92 | 92 |

TABLE 10

|  |  | Comparative Example 1 | Comparative Example 2 | Comparative Example 3 | Comparative Example 4 | Comparative Example 5 | Comparative Example 6 | Comparative Example 7 | Comparative Example 8 |
|---|---|---|---|---|---|---|---|---|---|
| Salt | SBPBF4 | 1.0M | 0.8M | 0.8M | 0.8M | 0 | 0 | 0 | 0 |
|  | TEABF4 | 0 | 0 | 0 | 0 | 1.0M | 0.8M | 0.8M | 0.8M |
| Solvent | Acetonitrile (vol %) | 100% | 100% | 97.5% | 95% | 100% | 100% | 97.5% | 95% |
|  | Sulfolane (vol %) |  |  | 2.5% | 5% |  |  | 2.5% | 5% |
|  | Amount of gas generated (ml) |  |  |  |  |  |  |  |  |
| Measurement results | 0 h | 0 | 0 | 0 | 0 | 0 | 0 | 0 | 0 |
|  | 250 h | 0.8 | 0.7 | 0.6 | 0.6 | 1.2 | 1.1 | 0.8 | 0.8 |

TABLE 10-continued

|  | Comparative Example 1 | Comparative Example 2 | Comparative Example 3 | Comparative Example 4 | Comparative Example 5 | Comparative Example 6 | Comparative Example 7 | Comparative Example 8 |
|---|---|---|---|---|---|---|---|---|
| 500 h | 1.6 | 1.4 | 1.2 | 1.2 | 2.3 | 2.1 | 1.4 | 1.4 |
| Initial performance (capacitance (F)) | 3.7 | 3.7 | 3.7 | 3.7 | 3.5 | 3.4 | 3.4 | 3.4 |
| Capacitance retention (%) |  |  |  |  |  |  |  |  |
| 0 h | 100 | 100 | 100 | 100 | 100 | 100 | 100 | 100 |
| 250 h | 91 | 93 | 94 | 94 | 83 | 80 | 83 | 83 |
| 500 h | 86 | 88 | 89 | 89 | 75 | 72 | 75 | 75 |

TABLE 11

|  |  | Example 55 | Example 56 | Example 57 | Example 58 | Example 59 | Example 60 |
|---|---|---|---|---|---|---|---|
| Salt | SBPBF4 | 0.8M | 0.8M | 0.8M | 0.8M | 0.8M | 0.8M |
|  | TEABF4 | 0 | 0 | 0 | 0 | 0 | 0 |
| Solvent | Acetonitrile (vol %) | 97.5% | 97.5% | 97.5% | 97.5% | 97.5% | 97.5% |
|  | Sulfolane (vol %) | 2.5% | 2.5% | 2.5% | 2.5% | 2.5% | 2.5% |
| Additive | 2,6-Di-tert-butylpyridine (mass %) | 0.0005 mass % | 0.05 mass % | 0.5 mass % | 0.75 mass % | 5.0 mass % | 7.5 mass % |
|  | Amount of gas generated (ml) |  |  |  |  |  |  |
| Measurement results | 0 h | 0 | 0 | 0 | 0 | 0 | 0 |
|  | 250 h | 0.5 | 0.4 | 0.3 | 0.3 | 0.4 | 1.0 |
|  | 500 h | 0.9 | 0.8 | 0.6 | 0.6 | 0.8 | 1.9 |
|  | Initial performance (capacitance (F)) | 3.7 | 3.7 | 3.7 | 3.7 | 3.7 | 3.7 |
|  | Capacitance retention (%) |  |  |  |  |  |  |
|  | 0 h | 100 | 100 | 100 | 100 | 100 | 100 |
|  | 250 h | 93 | 94 | 94 | 94 | 94 | 89 |
|  | 500 h | 88 | 89 | 89 | 89 | 89 | 83 |

The invention claimed is:

1. An electrolyte solution comprising:
a solvent;
a quaternary ammonium salt; and
a nitrogen-containing unsaturated cyclic compound,
the unsaturated cyclic compound being a nitrogen-containing unsaturated heterocyclic compound,
the unsaturated cyclic compound excluding salts of the unsaturated cyclic compound and ionic liquids obtainable from the unsaturated cyclic compound,
wherein the solvent contains 0.1 to 15 vol % of a sultone, a compound containing a sulfonyl group, a compound containing a sulfinyl group, a compound containing a sulfate group, or a compound containing sulfite group, and
wherein the quaternary ammonium salt is triethylmethylammonium tetrafluoroborate, tetraethylammonium tetrafluoroborate, or spirobipyrrolidinium tetrafluoroborate.

2. The electrolyte solution according to claim 1, wherein the unsaturated cyclic compound accounts for 0.0005 to 5 mass % relative to the electrolyte solution.

3. The electrolyte solution according to claim 1, wherein the unsaturated cyclic compound is at least one selected from the group consisting of pyrrole, pyridine, azirine, azepine, imidazole, pyrazole, oxazole, thiazole, imidazoline, pyrazine, thiazine, and indole, and any of these compounds containing a substituent.

4. The electrolyte solution according to claim 1, which is intended to be used for an electrochemical device.

5. The electrolyte solution according to claim 1, which is intended to be used for an electric double-layer capacitor.

6. An electrochemical device comprising:
the electrolyte solution according to claim 1;
a positive electrode; and
a negative electrode.

7. The electrochemical device according to claim 6, which is an electric double-layer capacitor.

* * * * *